United States Patent [19]

Schaum et al.

[11] 4,094,901

[45] June 13, 1978

[54] PROCESS FOR PREPARING ACETIC ACID

[75] Inventors: Helmut Schaum, Bad Soden am Taunus; Friedrich Schenk, Gotzenhain; Hartmut Voigt, Tarragona; Rudolf Sartorius, Frankfurt am Main, all of Germany

[73] Assignee: Hoechst Aktiengesellschaft, Frankfurt am Main, Germany

[21] Appl. No.: 671,442

[22] Filed: Mar. 29, 1976

[30] Foreign Application Priority Data

Mar. 29, 1975 Germany .............................. 2514095

[51] Int. Cl.$^2$ ............................................. C07C 51/26
[52] U.S. Cl. ................................................ 260/530 R
[58] Field of Search .................................... 260/530 R

[56] References Cited

U.S. PATENT DOCUMENTS

| 2,425,880 | 8/1947 | Hull ................................. 260/530 R |
| 2,425,882 | 8/1947 | Hull ................................. 260/530 R |
| 3,871,971 | 3/1975 | Schaum et al. ................... 260/530 R |

FOREIGN PATENT DOCUMENTS

38-14,712  8/1963  Japan .............................. 260/530 R

*Primary Examiner*—Vivian Garner
*Attorney, Agent, or Firm*—Curtis, Morris & Safford

[57] ABSTRACT

Process for preparing acetic acid by oxidation of acetaldehyde with oxygen or oxygen containing gases in the presence of a catalyst based on manganese acetate, wherein the crude acetic acid and the gases formed, still containing acetaldehyde, are submitted to an after-oxidation, the low-boiling substances are distilled off and the residue is reused as catalyst.

5 Claims, 1 Drawing Figure

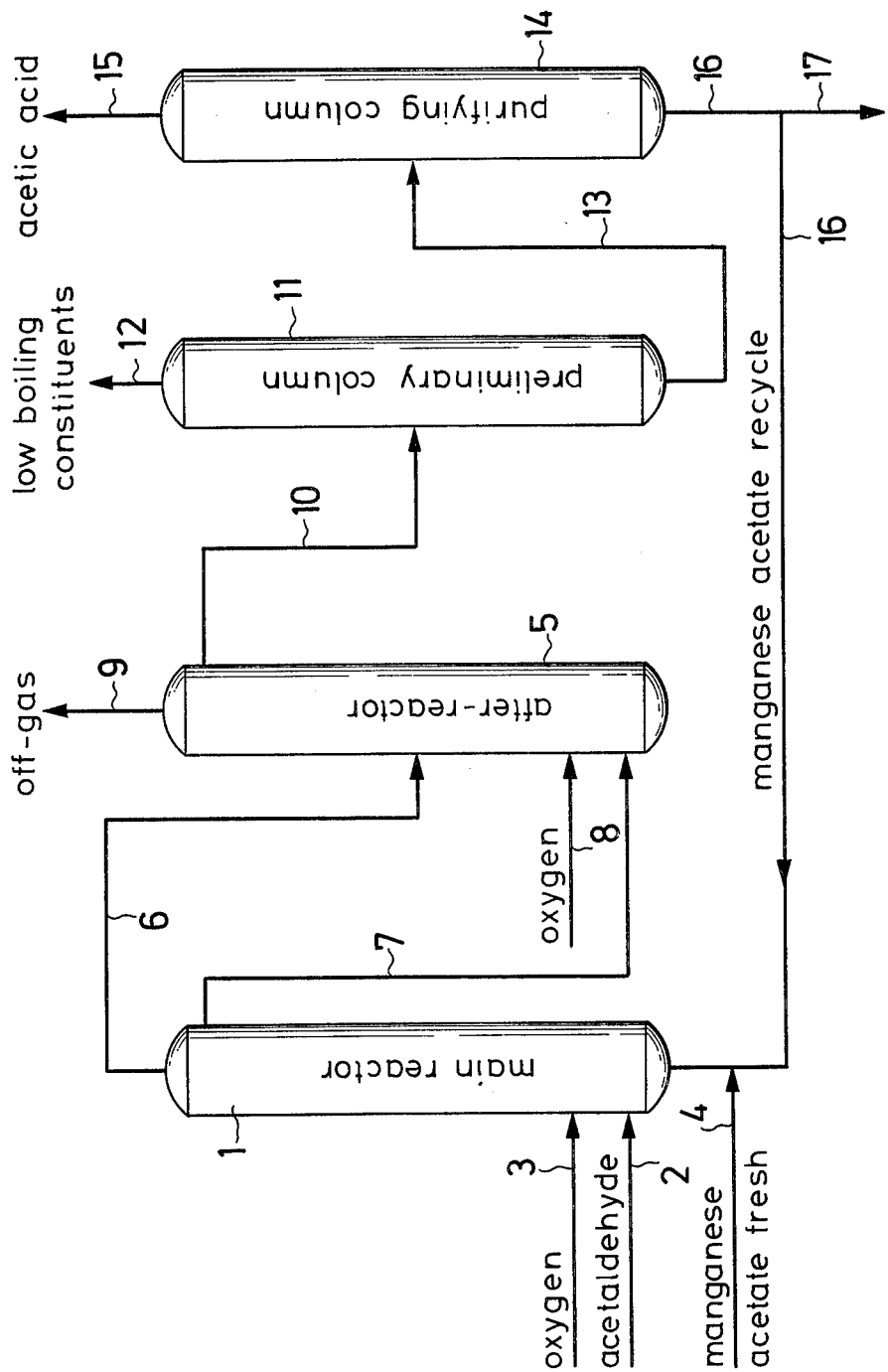

PROCESS FOR PREPARING ACETIC ACID

Acetic acid is prepared generally in the industry by catalytical oxidation of acetaldehyde with oxygen by using manganese acetate as catalyst.

This reaction is generally regulated such that about 4% of acetaldehyde are not reacted and recycled subsequently to the reaction after having been separated from the crude acetic acid.

The fraction having the next higher boiling point consists substantially of acetic acid. The remaining bottom product contains the used manganese acetate catalyst, acetic acid and high boiling by-products, such as acetylated aldehydes (for example ethylidene diacetate), acetylated oxidation products of acetic acid (for example acetoxyglycolic acid ester), oxidation products of acetic acid (for example succinic acid derivatives) and condensation products of acetic acid (for example acetoacetic acid derivatives). This liquid containing manganese acetate cannot be reused without difficulty as catalyst, as the reaction ceases after a short time when using such as mixture.

It has now been found surprisingly that this residue may be reused as a catalyst by submitting the crude acetic acid formed in the reaction and containing generally of from 1 to 10% of acetaldehyde to an oxidative after-reaction with oxygen or gases containing oxygen.

The process according to the invention for preparing acetic acid by oxidation of acetaldehyde with oxygen or oxygen containing gases in the presence of a manganese acetate catalyst comprises submitting the crude acetic acid prepared from acetaldehyde in known manner and still containing from 1 to 10% by weight of acetaldehyde together with the gases containing acetaldehyde, which are formed in the acetic acid synthesis, to an after-oxidation with oxygen or with oxygen containing gases, distilling off the low-boiling by-products and acetic acid and reusing as catalyst the residue comprising manganese acetate, high boiling by-products and acetic acid.

The residue containing manganese acetate, high boiling by-products and acetic acid may be reused without difficulty in the oxidation of acetaldehyde yielding acetic acid.

The acetic acid synthesis and the oxidative after-reaction are generally performed under a pressure from 1 to 20 atmospheres, preferably from 1 to 2 atmospheres and at a temperature from 35° to 150° C, preferably from 40° to 90° C.

A substantial advantage of the process according to the invention resides in the fact that the recovery of acetaldehyde may be dispensed with. For carrying out the process of the invention the following procedure, as illustrated in the accompanying drawing, has proved especially advantageous.

Referring to the drawing:

Into the main reactor 1 there are introduced acetaldehyde via conduit 2, oxygen via conduit 3 and manganese acetate via conduit 4. The reaction products and unreacted starting material are transferred to the afterreactor 5, i.e. the gaseous substances (principally carbon dioxide and vaporous unreacted acetaldehyde) via conduit 6 and the liquid substances (acetic acid, unreacted acetaldehyde, water, by-products, manganese acetate) via conduit 7. Oxygen is introduced into the afterreactor via conduit 8 for the after-oxidation of unreacted acetaldehyde. A waste gas mainly consisting of carbon dioxide is removed via conduit 9. A mixture of acetic acid, water, by-products and manganese acetate free from acetaldehyde is transferred to the column 11 via conduit 10. The low-boiling by-products (mainly methyl acetate, methyl formiate, methanol and water) are distilled off in said column via conduit 12. Acetic acid, high-boiling by-products and manganese acetate are transferred via conduit 13 to the column 14. Acetic acid is distilled off in said column as head product via conduit 15. The high-boiling by-products and manganese acetate (dissolved in acetic acid) leave the column 14 via conduit 16 and are recycled to the main reactor 1, optionally after elimination of a part of the high-boiling by-products and separation of insoluble residues via conduit 17.

The following examples illustrate the invention:

EXAMPLE:

The test arrangement corresponded to the accompanying drawing. To the reactor 1, containing in a stationary state 1.2 kg of $Mn(OOCCH_3)_2 \cdot 4 H_2O$ there were fed 764 kg/h of acetaldehyde via conduit 2, 185 N m$^3$/h of oxygen (N meaning under normal conditions of pressure and temperature, i.e. 760 mm Hg and 0° C) via conduit 3 and 0.06 kg/h of fresh manganese acetate via conduit 4. The temperature and the pressure in the reactor were 60° C and 1 atmosphere respectively. 20 N m$^3$/h of oxygen were fed to the afterreactor 5 via conduit 8 and the reaction products from the reactor 1 via conduits 6 and 7. The waste gases withdrawn via conduit 9 were burnt. The low-boiling products contained in the bottom product of the afterreactor 5 were separated in column 11 and acetic acid in column 14. 1000 kg/h of acetic acid were obtained via conduit 15 which corresponded to a yield of 96%, calculated on acetaldehyde charged. The bottom product of column 14 was withdrawn via conduit 16 and was recycled to the reactor 1 and reused as catalyst. The yield of acetic acid remained constant over a period of 8 weeks.

COMPARATIVE EXAMPLE

The test arrangement corresponded to that of the accompanying drawing, but there was not used an afterreactor 5. The gaseous substances (mainly carbon dioxide and unreacted gaseous acetaldehyde) were removed from the main reactor 1 via conduit 6 as waste gases. The liquid substances (acetic acid, unreacted acetaldehyde, water, by-products, manganese acetate) were transferred to the column 11 via conduit 7 directly from the main reactor 1.

205 N m$^3$/h of oxygen were fed to the reactor 1 via conduit 2 and 1.2 kg/h of $Mn(OOCCH_3)_2 \cdot 4 H_2O$ via conduit 4. The reaction temperature in the reactor 1 was 60° C, the pressure 1 atmosphere. The liquid products still containing 4% of acetaldehyde which had been transferred via conduit 7 were distilled in the column 11, while the low-boiling products were removed via conduit 12. The acetaldehyde contained in the latter products was isolated and recycled to the reactor 1. The bottom product of the column 11 was transferred to the column 14 via conduit 13. 1000 kg/h of acetic acid were obtained via conduit 15. This corresponded to a yield of 94.7% by weight, calculated on acetaldehyde charged.

When recycling to reactor 1 the bottom product of column 14 containing manganese acetate the reaction ceased after a short time.

What is claimed is:

1. A process for preparing acetic acid by oxidation of acetaldehyde with oxygen or oxygen containing gases in the presence of a manganese acetate catalyst, which comprises subjecting the crude acetic acid prepared by said oxidation of acetaldehyde and still containing from 1 to 10% by weight of acetaldehyde, together with the gases formed in the acetic acid synthesis and still containing acetaldehyde, to an afteroxidation with oxygen or oxygen containing gases, distilling off the low-boiling by-products and acetic acid and directly recycling for reuse as catalyst in the initial oxidation the residue comprising manganese acetate, high-boiling by-products and acetic acid.

2. The process as defined in claim 1, which comprises performing the afteroxidation at a pressure of from 1 to 20 atmospheres gauge.

3. The process as defined in claim 2, wherein the afteroxidation is performed at a pressure of from 1 to 2 atmospheres.

4. The process as defined in claim 1, which comprises performing the afteroxidation at a temperature of from 35° to 150° C.

5. The process as defined in claim 4, wherein the afteroxidation is performed at a temperature of from 40° to 90° C.

* * * * *